United States Patent
Sedat et al.

(10) Patent No.: US 9,018,429 B2
(45) Date of Patent: Apr. 28, 2015

(54) PROCESS FOR THE PREPARATION OF FLUOROOLEFIN COMPOUNDS

(75) Inventors: Pierre-Marie Sedat, Fleurieux sur l'Arbresle (FR); Jean-Michel Bossoutrot, Chaponost (FR)

(73) Assignee: Arkenna France, Colombes (FR)

( * ) Notice: Subject to any disclaimer, the term of this patent is extended or adjusted under 35 U.S.C. 154(b) by 186 days.

(21) Appl. No.: 13/144,239

(22) PCT Filed: Jan. 12, 2010

(86) PCT No.: PCT/FR2010/050043
§ 371 (c)(1),
(2), (4) Date: Oct. 3, 2011

(87) PCT Pub. No.: WO2010/081988
PCT Pub. Date: Jul. 22, 2010

(65) Prior Publication Data
US 2012/0022301 A1    Jan. 26, 2012

(30) Foreign Application Priority Data
Jan. 13, 2009   (FR) ..................................... 09 50157

(51) Int. Cl.
*C07C 17/25* (2006.01)
*C07C 19/08* (2006.01)
(Continued)

(52) U.S. Cl.
CPC ............... *C07C 17/25* (2013.01); *C07C 17/383* (2013.01)

(58) Field of Classification Search
None
See application file for complete search history.

(56) References Cited

U.S. PATENT DOCUMENTS

| 4,414,185 | A | 11/1983 | Harrison |
| 6,548,719 | B1 | 4/2003 | Van Der Puy et al. |
| 2010/0121115 | A1 | 5/2010 | Rao et al. |

(Continued)

FOREIGN PATENT DOCUMENTS

| JP | 53-078999 A | 7/1978 |
| JP | 2004018308 | 1/2004 |

(Continued)

OTHER PUBLICATIONS

Office Action dated Apr. 4, 2013 for U.S. Appl. No. 13/384,256.
(Continued)

*Primary Examiner* — Clinton Brooks
(74) *Attorney, Agent, or Firm* — Brinks Gilson & Lione

(57) ABSTRACT

The subject of the invention is a process for the preparation of fluoroolefin compounds. It relates more particularly to a process for manufacturing a (hydro)fluoroolefin compound comprising (i) bringing at least one compound comprising from three to six carbon atoms, at least two fluorine atoms and at least one hydrogen atom, provided that at least one hydrogen atom and one fluorine atom are located on adjacent carbon atoms, into contact with potassium hydroxide in a stirred reactor, containing an aqueous reaction medium, equipped with at least one inlet for the reactants and with at least one outlet, in order to give the (hydro)fluoroolefin compound, which is separated from the reaction medium in gaseous form, and potassium fluoride, (ii) bringing the potassium fluoride formed in (i) into contact, in an aqueous medium, with calcium hydroxide in order to give potassium hydroxide and to precipitate calcium fluoride, (iii) separation of the calcium fluoride precipitated in step (ii) from the reaction medium and (iv) optionally, the reaction medium is recycled after optional adjustment of the potassium hydroxide concentration to step (i).

16 Claims, 1 Drawing Sheet

(51) Int. Cl.
*C07C 21/18* (2006.01)
*C07C 17/383* (2006.01)

(56) References Cited

U.S. PATENT DOCUMENTS

| | | |
|---|---|---|
| 2010/0145111 A1 | 6/2010 | Sharratt et al. |
| 2010/0185029 A1 | 7/2010 | El Sheikh et al. |

FOREIGN PATENT DOCUMENTS

| | | |
|---|---|---|
| SU | 0 709 537 | 1/1980 |
| WO | WO 03/027051 | 4/2003 |
| WO | WO 2007/056194 | 5/2007 |
| WO | WO 2007/144665 | 12/2007 |
| WO | 2008/030439 | 3/2008 |
| WO | 2008/030440 | 3/2008 |
| WO | WO 2008/075017 | 6/2008 |
| WO | WO 2009/003157 | 12/2008 |
| WO | 2009/138764 | 11/2009 |

OTHER PUBLICATIONS

Final Office Action dated Oct. 31, 2013 for U.S. Appl. No. 13/384,256.
Sianesi, Dario XP009092725 Fluoroolefine—Nota I. Cis e trans 1,2,3,3,3- Pentafluoropropilence. pp. 850-861.
Nouveau Traite De Chimie Minerale—Publie Sous La Direction De—Paul Pascal—Tome II—Deuxieme Fascicule—Masson Et Cie, Editeurs 1963.
WPI Thompson—XP-002568903—Thompson Scientific, London GB; AN—1980-61936C—LOPATKINA.
Kyunyants et al., Journal of the USSR Academy of Science Chemistry Dept. Fluoroolefin Reactions Report 13, "Catalytic Hydrogenation of Perfluoroolefins" (1960).
International Search Report for International Application No. PCT/FR2010/050043, dated Apr. 13, 2010.

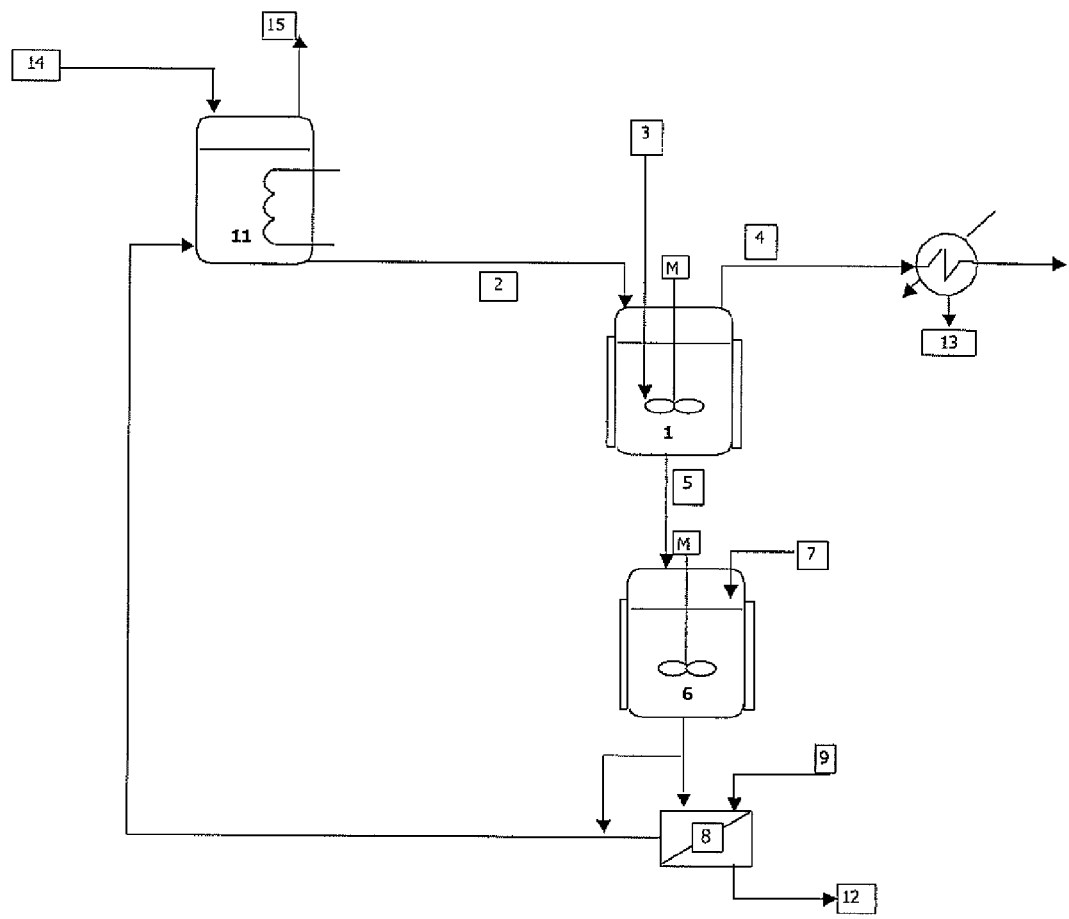

PROCESS FOR THE PREPARATION OF FLUOROOLEFIN COMPOUNDS

CROSS-REFERENCE TO RELATED APPLICATIONS

This application is the U.S. National Phase of International Application No. PCT/FR2010/050043, filed Jan. 12, 2010, which claims priority to French Application No. FR 0950157, filed Jan. 13, 2009.

FIELD OF THE INVENTION

The subject of the invention is a process for the preparation of fluoroolefin compounds. The invention relates more particularly to a process for the preparation of hydrofluoropropenes.

TECHNOLOGICAL BACKGROUND

Hydrofluorocarbons (HFCs) and in particular hydrofluoroolefins (HFOs), such as 2,3,3,3-tetrafluoro-1-propene (HFO-1234yf), are compounds known for their properties of refrigerants and heat-exchange fluids, extinguishers, propellants, foaming agents, blowing agents, gaseous dielectrics, polymerization medium or monomer, support fluids, agents for abrasives, drying agents and fluids for energy production units. Unlike CFCs and HCFCs, which are potentially dangerous to the ozone layer, HFOs do not comprise chlorine and thus do not present a problem for the ozone layer.

1,2,3,3,3-Pentafluoropropene (HFO-1225ye) is a synthetic intermediate in the manufacture of 2,3,3,3-tetrafluoro-1-propene (FIFO-1234yf).

The majority of the processes for the manufacture of hydrofluoroolefins involve a dehydrohalogenation reaction. Thus, the document WO 03/027051 describes a process for the manufacture of fluoroolefins of formula $CF_3CY=CX_nH_p$, in which X and Y each represent a hydrogen atom or a halogen atom chosen from fluorine, chlorine, bromine or iodine and n and p are integers and can independently take the value zero, 1 or 2, provided that $(n+p)=2$, which comprises bringing a compound of formula $CF_3C(R^1_aR^2_b)C(R^3_cR^4_d)$, with $R^1$, $R^2$, $R^3$ and $R^4$ independently representing a hydrogen atom or a halogen atom chosen from fluorine, chlorine, bromine or iodine, provided that at least one of $R^1$, $R^2$, $R^3$ and $R^4$ is a halogen atom and that at least one hydrogen atom and one halogen atom are situated on adjacent carbon atoms, a and b being able independently to take the value zero, 1 or 2, provided that $(a+b)=2$, and c and d being able independently to take the value zero, 1, 2 or 3, provided that $(c+d)=3$, into contact with at least one alkali metal hydroxide in the presence of a phase transfer catalyst.

This document teaches, in Example 2, that, in the absence of a phase transfer catalyst, there is no reaction when 1,1,1,3,3-pentafluoropropane (HFC-245fa) is brought into contact with a 50% by weight aqueous potassium hydroxide (KOH) solution at ambient temperature and under pressure for 24 hours.

In addition, this document teaches a reaction temperature of between −20° C. and 80° C.

The document WO 2008/075017 illustrates the dehydrofluorination reaction of 1,1,1,2,3,3-hexafluoropropane (HFC-236ea) to give 1,2,3,3,3-pentafluoropropene (HFO-1225ye) at 150° C. in the presence of a 50% by weight aqueous KOH solution. In the absence of a phase transfer catalyst, the conversion after 3 and a half hours is 57.8% and the selectivity for HFO-1225ye is 52.4% (Test 1). In the presence of a phase transfer catalyst, this conversion is reached after only 2.5 hours and the selectivity is virtually unchanged (Test 4). As indicated in Table 2 of this document, it is necessary to use an organic solvent in order to increase the selectivity for HFO-1225ye.

WO 2007/056194 describes the preparation of HFO-1234yf by dehydrofluorination of 1,1,1,2,3-pentafluoropropane (HFC-245eb) either with an aqueous KOH solution or in the gas phase in the presence of a catalyst, in particular over a catalyst based on nickel, carbon or a combination of these.

The document Knunyants et al., Journal of the USSR Academy of Sciences, Chemistry Department, "Fluoroolefin Reactions", Report 13, "Catalytic Hydrogenation of Perfluoroolefins", 1960, clearly describes various chemical reactions on fluorinated compounds. This document describes the dehydrofluorination of 1,1,1,2,3,3-hexafluoropropane (236ea) by passing through a suspension of KOH powder in dibutyl ether, to produce 1,2,3,3,3-pentafluoro-1-propene (HFO-1225ye) with a yield of only 60%. This document also describes the dehydrofluorination of 1,1,1,2,3-pentafluoropropane (HFC-245eb) to give 2,3,3,3-tetrafluoro-1-propene (HFO-1234yf) by passing into a suspension of KOH powder in dibutyl ether with a yield of only 70%.

Furthermore, FIG. 2 on page 51 of Part 2 of the nouveau traité de chimie minérale [New Treatise on Inorganic Chemistry] by P. Pascal, Ed. 1963, shows the appearance of the liquid/solid equilibria of the water and potassium hydroxide system and the measurements are collated in the Table on page 52.

The dehydrofluorination reactions such as described above result, besides the desired hydrofluoroolefin compound, in the formation of water and potassium fluoride. Furthermore, the implementation of such a reaction in continuous mode is not easy on an industrial scale since at least three phases (gas, liquid and solid) are involved.

SUMMARY OF THE INVENTION

The present invention provides a process for the continuous and semi-continuous manufacture of a (hydro)fluoroolefin compound that makes it possible to overcome the aforementioned drawbacks.

The subject of the present invention is therefore a process for the continuous or semi-continuous manufacture of a (hydro)fluoroolefin compound comprising (i) bringing at least one compound comprising from three to six carbon atoms, at least two fluorine atoms and at least one hydrogen atom, provided that at least one hydrogen atom and one fluorine atom are located on adjacent carbon atoms, into contact with potassium hydroxide in a stirred reactor, containing an aqueous reaction medium, equipped with at least one inlet for the reactants and with at least one outlet, in order to give the (hydro)fluoroolefin compound, which is separated from the reaction medium in gaseous form, and potassium fluoride, (ii) bringing the potassium fluoride formed in (i) into contact, in an aqueous medium, with calcium hydroxide in order to give potassium hydroxide and to precipitate calcium fluoride, (iii) separation of the calcium fluoride precipitated in step (ii) from the reaction medium and (iv) optionally, the reaction medium is recycled after optional adjustment of the potassium hydroxide concentration to step (i).

The present invention thus makes it possible to obtain an advantageous process since, on the one hand, potassium hydroxide is more reactive than calcium hydroxide in the dehydrofluorination reaction and, on the other hand, calcium fluoride is a reusable by-product.

The process according to the present invention preferably provides a (hydro)fluoroolefin compound comprising three carbon atoms, advantageously a (hydro)fluoroolefin compound represented by the formula (I):

$$CF_3CY=CX_nH_p \qquad (I)$$

in which Y represents a hydrogen atom or a halogen atom chosen from fluorine, chlorine, bromine or iodine and X represents a halogen atom chosen from fluorine, chlorine, bromine or iodine; n and p are integers and may independently take the value zero, 1 or 2 provided that (n+p)=2, by bringing a compound of formula $CF_3CYRCR'X_nH_p$, in which X, Y, n and p have the same meaning as in formula (I) and R represents a fluorine atom when R' represents a hydrogen atom or R represents a hydrogen atom when R' represents a fluorine atom into contact with potassium hydroxide.

The present invention is very particularly suitable for the manufacture of a compound of formula (Ia):

$$CF_3\text{—}CF=CHZ \qquad (Ia)$$

in which Z represents a hydrogen or fluorine atom, from a compound of formula $CF_3CFRCHR'Z$, in which Z has the same meaning as in formula (Ia) and R represents a fluorine atom when R' represents a hydrogen atom or R represents a hydrogen atom when R' represents a fluorine atom.

Thus, 2,3,3,3-tetrafluoropropene may be obtained by dehydrofluorination of 1,2,3,3,3-pentafluoropropane with KOH and/or 1,2,3,3,3-pentafluoropropene by dehydrofluorination of 1,1,1,2,3,3-hexafluoropropane with KOH. The 1,2,3,3,3-pentafluoropropene may be in the cis and/or trans isomer form.

The present invention may also be used for the manufacture of 1,3,3,3-tetrafluoropropene by dehydrofluorination of 1,1,3,3,3-pentafluoropropane with KOH.

DETAILED DESCRIPTION OF PREFERRED EMBODIMENTS

In the remainder of the text, the limits of the concentration and temperature ranges given are included in said ranges.

In step (i) of the process according to the present invention, the potassium hydroxide may represent between 10 and 90% by weight relative to the weight of the water and KOH mixture present in the aqueous reaction medium, preferably between 20 and 86% and advantageously between 55 and 75% by weight. Depending on the content, the potassium hydroxide may be in the form of an aqueous solution or in the molten state. This high KOH content leads to an increase in the conversion rate of the hydrofluoroalkane to hydrofluoroalkene. Moreover, due to this concentrated KOH medium, the HF formed in (i) reacts immediately with KOH to form KF that is less corrosive than HF, which makes it possible to use, downstream of the dehydrofluorination reactor, carbon steel reactors that are of low cost compared to reactors made of an inert material (UB6 or Inconel) for the dehydrofluorination reactor. Moreover, the "trapping" of HF in the form of KF facilitates the separation of the various products from one another (HF having a tendency to form azeotropes with hydrofluoroalkanes and hydrofluoroalkenes), thus, a simple distillation is sufficient to separate the products from one another.

The step (i) is generally carried out at a temperature such that the water formed during the dehydrofluorination reaction is removed, partly or completely, from the reaction medium via entrainment of the gas stream comprising the (hydro) fluoroolefin compound from the stirred reactor. This temperature is preferably between 80 and 180° C., advantageously between 125 and 180° C., and very particularly between 145 and 165° C. The evaporation of the water during step (i) is in the direction of increasing the conversion rate of the hydrofluoroalkane to hydrofluoroalkene.

The dehydrofluorination reaction of step (i) may be carried out at atmospheric pressure, but it is preferred to work at a pressure above atmospheric pressure. Advantageously, this pressure is between 1.1 and 2.5 bar.

The reaction of step (ii) may be carried out in a stirred reactor or fluidized bed reactor by reacting calcium hydroxide, preferably in a suspension in water, with the potassium fluoride from step (i). The reaction temperature may vary to a large extent but for economic reasons, it is preferably between 50 and 150° C., for example from 75° C. to 120° C. and advantageously between 90 and 120° C.

When a suspension of calcium hydroxide is used in step (ii), the calcium hydroxide represents between 2 and 40% by weight relative to the weight of the suspension.

Advantageously, step (ii) is carried out in the reaction medium from step (i) comprising water, potassium hydroxide and potassium chloride. The potassium fluoride originating from step (i) and supplying step (ii) may be dissolved or in suspension.

The potassium hydroxide represents, in the reaction medium of step (ii), preferably between 2 and 50% by weight relative to the weight of the water and potassium hydroxide mixture of the medium.

When the steps (i) and (ii) are carried out in separate reactors, it is possible to provide a dilution step of the reaction medium between step (1) and step (ii).

The calcium fluoride precipitated in step (ii) is separated from the reaction medium, for example by filtration and/or settling. Prior to the filtration, it is possible to provide a settling step. The calcium fluoride thus separated is then washed with water.

During the settling step, it is possible to make provision for the recycling of a portion of the suspension that is concentrated in calcium fluoride to step (ii). Advantageously, the content of calcium fluoride solids present in the reaction medium of step (ii) is between 5 and 40% by weight.

After separation of the calcium fluoride, the reaction medium with or without the calcium fluoride washing waters may be recycled to step (i) after optional adjustment of the potassium hydroxide content.

According to one embodiment of the invention, steps (i) and (ii) may be carried out in the same reactor.

It may be advantageous to use an inert gas, preferably nitrogen or hydrogen in the dehydrofluorination step.

The process according to the present invention has the advantage of resulting in high yields even in the absence of a phase transfer catalyst and/or an organic solvent.

The present invention also comprises the combinations of the preferred forms regardless of the embodiment.

EXPERIMENTAL SECTION

Example 1

FIG. 1 gives the diagram for one embodiment of the present invention. A stirred reactor (1), made of nickel, equipped with a device for heating and measuring the temperature of the reaction medium, containing a mixture of water and of KOH, is continuously fed with a solution of molten KOH (2) in which the KOH is present at 60% by weight in the water, and with 1,1,1,2,3,3-hexafluoropropane (3). The temperature is kept at 160° C. and the pressure in the reactor is 1.2 bar absolute. The gaseous products exit the reactor via an orifice (4) located in the cover of the reactor and the water contained in the gas stream is removed by condensation (13).

The outlet (5) of the reactor (I) is connected to the inlet of the stirred reactor (6) and therefore provides the reactor (6) with the supply of potassium hydroxide, which may be in suspension in the aqueous medium. A 10% by weight suspension of calcium hydroxide in water is introduced into the reactor (6) via the line (7). The reactor (6) is kept at a temperature between 100 and 120° C.

The outlet of the reactor (6) is connected to a filter (8) in order to separate the calcium fluoride from the reaction medium, then wash it with water introduced via the line (9); the aqueous medium separated from the calcium fluoride and also the calcium fluoride washing waters are then recycled to the reactor (1) after adjustment of the KOH concentration; the calcium fluoride is recovered via the line (12).

The mixture of molten KOH supplying the reactor (1) is prepared by heating (11) an aqueous solution of 50% by weight of KOH introduced by the line (14) for the purposes of evaporation (removal of water (15)).

Example 2

The procedure of example 1 is followed except that the reactor (1) is continuously supplied with 1,2,3,3,3-pentafluoropropane instead of 1,1,1,2,3,3-hexafluoropropane.

By using a KOH content higher than that from the prior art, improved conversion rates of the hydrofluoroalkane to hydrofluoroalkene (therefore a better productivity), a reusable produce, $CaF_2$, and lower manufacturing costs of the hydrofluoroalkene are obtained.

The invention claimed is:

1. A process for the continuous or semi-continuous manufacture of a (hydro)fluoroolefin compound of the formula $CF_3$—CF=CHZ wherein Z is a hydrogen or fluorine atom, comprising:
   (i) reacting at least one reactant compound with potassium hydroxide in a stirred reactor comprising an aqueous reaction medium, wherein:
      said at least one reactant compound is of the formula $CF_3CFRCHR'Z$, wherein Z is a hydrogen or fluorine atom and R is a fluorine atom and R' is a hydrogen atom or R is a hydrogen atom and W is a fluorine atom, and
      the amount of potassium hydroxide in the aqueous reaction medium in step (i) represents between 55 and 90% by weight relative to the weight of water and potassium hydroxide in the aqueous reaction medium;
   to yield:
      said (hydro)fluoroolefin compound, wherein the (hydro)fluoroolefin compound is separated from the aqueous reaction medium in gaseous form, and
      potassium fluoride
   (ii) reacting said potassium fluoride with calcium hydroxide in an aqueous reaction medium of step (ii) to yield potassium hydroxide and calcium fluoride precipitate; and
   (iii) separating the calcium fluoride precipitate from the aqueous reaction medium.

2. The process of claim 1, further comprising: (iv) recycling the aqueous reaction medium from step (ii) to step (i).

3. The process of claim 2, further comprising adjusting the potassium hydroxide concentration of the aqueous reaction medium of step (ii) before recycling to step (i).

4. The process of claim 1, wherein:
   the (hydro)fluoroolefin compound comprises 2,3,3,3-tetrafluoropropene and the reactant compound comprises 1,2,3,3,3-pentafluoropropane, or
   the (hydro)fluoroolefin compound comprises 1,2,3,3,3-pentafluoropropene and the reactant compound comprises 1,1,1,2,3,3-hexafluoropropane.

5. The process of claim 1, wherein the operating temperature of step (i) ranges from 80° C. to 180° C.

6. The process of claim 5, wherein the operating temperature of step (i) ranges from 125° C. to 180° C.

7. The process of claim 6, wherein the operating temperature of step (i) ranges from 145° C. to 165° C.

8. The process of claim 1, wherein the temperature of step (ii) ranges from 50° C. to 150° C.

9. The process of claim 8, wherein the temperature of step (ii) ranges from 75° C. to 120° C.

10. The process of claim 9, wherein the temperature of step (ii) ranges from 90° C. to 120° C.

11. The process of claim 1, wherein step (ii) is carried out in the aqueous reaction medium of step (i).

12. The process of claim 1, wherein the amount of potassium hydroxide in the aqueous medium of step (ii) ranges from 2% to 50% by weight relative to the weight of water and potassium hydroxide.

13. The process of claim 1, wherein separating the calcium fluoride precipitate from the aqueous reaction medium comprises filtering the calcium fluoride.

14. The process of claim 13, further comprising allowing the calcium fluoride to settle before filtering.

15. The process of claim 14, further comprising recycling a portion of a suspension concentrated in calcium fluoride to step (ii) during the settling step.

16. The process of claim 1, wherein the concentration of calcium fluoride solids in the reaction medium of step (ii) is between 5 and 40% by weight.

* * * * *

UNITED STATES PATENT AND TRADEMARK OFFICE
CERTIFICATE OF CORRECTION

PATENT NO. : 9,018,429 B2  
APPLICATION NO. : 13/144239  
DATED : April 28, 2015  
INVENTOR(S) : Sedat et al.

Page 1 of 1

It is certified that error appears in the above-identified patent and that said Letters Patent is hereby corrected as shown below:

Title Page

(73) Assignee: please change "Arkenna France" to --Arkema France--; and

In the Claims

Column 5, claim 1, line 43, please change "W" to --R'--.

Signed and Sealed this
Fifteenth Day of September, 2015

Michelle K. Lee
*Director of the United States Patent and Trademark Office*